(12) United States Patent
Cheney

(10) Patent No.: US 12,414,600 B2
(45) Date of Patent: *Sep. 16, 2025

(54) MOTION-ASSIST FOOTWEAR COMPRISING A FORCE TRANSLATOR

(71) Applicant: FAST IP, LLC, Lindon, UT (US)

(72) Inventor: Craig Cheney, Lindon, UT (US)

(73) Assignee: FAST IP, LLC, Lindon, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/407,182

(22) Filed: Jan. 8, 2024

(65) Prior Publication Data

US 2024/0138515 A1    May 2, 2024

Related U.S. Application Data

(63) Continuation of application No. 17/827,949, filed on May 30, 2022, now Pat. No. 11,864,630, which is a continuation of application No. PCT/US2021/060404, filed on Nov. 22, 2021.

(60) Provisional application No. 63/116,379, filed on Nov. 20, 2020.

(51) Int. Cl.
| | |
|---|---|
| A43B 7/20 | (2006.01) |
| A43B 3/00 | (2022.01) |
| A43B 7/32 | (2006.01) |
| A61H 1/02 | (2006.01) |
| A61H 3/00 | (2006.01) |

(52) U.S. Cl.
CPC .............. *A43B 7/20* (2013.01); *A43B 3/0057* (2013.01); *A43B 7/32* (2013.01); *A61H 1/0266* (2013.01); *A61H 3/00* (2013.01); *A61H 2003/007* (2013.01); *A61H 2201/14* (2013.01); *A61H 2201/164* (2013.01); *A61H 2201/165* (2013.01)

(58) Field of Classification Search
CPC ........... A43B 7/20; A43B 3/0057; A43B 7/32; A61H 1/0266
USPC .................................................. 36/7.8, 25 R
See application file for complete search history.

(56) References Cited

U.S. PATENT DOCUMENTS

| | | | | |
|---|---|---|---|---|
| 979,243 | A * | 12/1910 | Anderson | A63B 22/001 482/51 |
| 2,440,894 | A * | 5/1948 | Caesar | A61F 5/0113 602/29 |
| 3,589,359 | A * | 6/1971 | Hill | A43B 7/20 602/28 |
| 3,859,991 | A * | 1/1975 | Theodores | A61F 5/0113 602/28 |
| 4,459,980 | A * | 7/1984 | Perser | A61F 5/0113 602/27 |
| 5,090,138 | A * | 2/1992 | Borden | A43B 7/20 36/102 |
| 5,475,935 | A * | 12/1995 | Frost | A43B 7/20 36/114 |
| 6,397,496 | B1 * | 6/2002 | Seymour | A63B 25/10 482/79 |
| 8,061,059 | B2 * | 11/2011 | Bruce | A43B 13/143 36/31 |
| 10,638,810 | B1 * | 5/2020 | Cheney | A43B 21/26 |
| 11,864,630 | B2 * | 1/2024 | Cheney | A61F 5/0127 |

(Continued)

*Primary Examiner* — Marie D Bays

(57) ABSTRACT

A motion-assist shoe having a force translator with a dynamic portion comprised of a resiliently deformable material and configured to bias a rearward portion of a sole portion of the shoe upward relative to a forward portion of the sole portion.

18 Claims, 3 Drawing Sheets

(56) References Cited

U.S. PATENT DOCUMENTS

| | | | |
|---|---|---|---|
| 2005/0126044 A1* | 6/2005 | Langley | A43B 19/00 36/89 |
| 2009/0000150 A1* | 1/2009 | Wong | A43B 7/14 36/89 |
| 2009/0217551 A1* | 9/2009 | Shirokikh | A63B 25/10 36/102 |
| 2010/0319215 A1* | 12/2010 | Roser | A43C 1/00 36/27 |
| 2011/0040225 A1* | 2/2011 | Gibbons | A63B 21/055 482/79 |
| 2012/0000095 A1* | 1/2012 | Torrance | A43B 13/16 36/114 |
| 2012/0159815 A1* | 6/2012 | Dekovic | A43B 13/16 36/103 |
| 2020/0015543 A1* | 1/2020 | Roser | A43B 23/0205 |

* cited by examiner

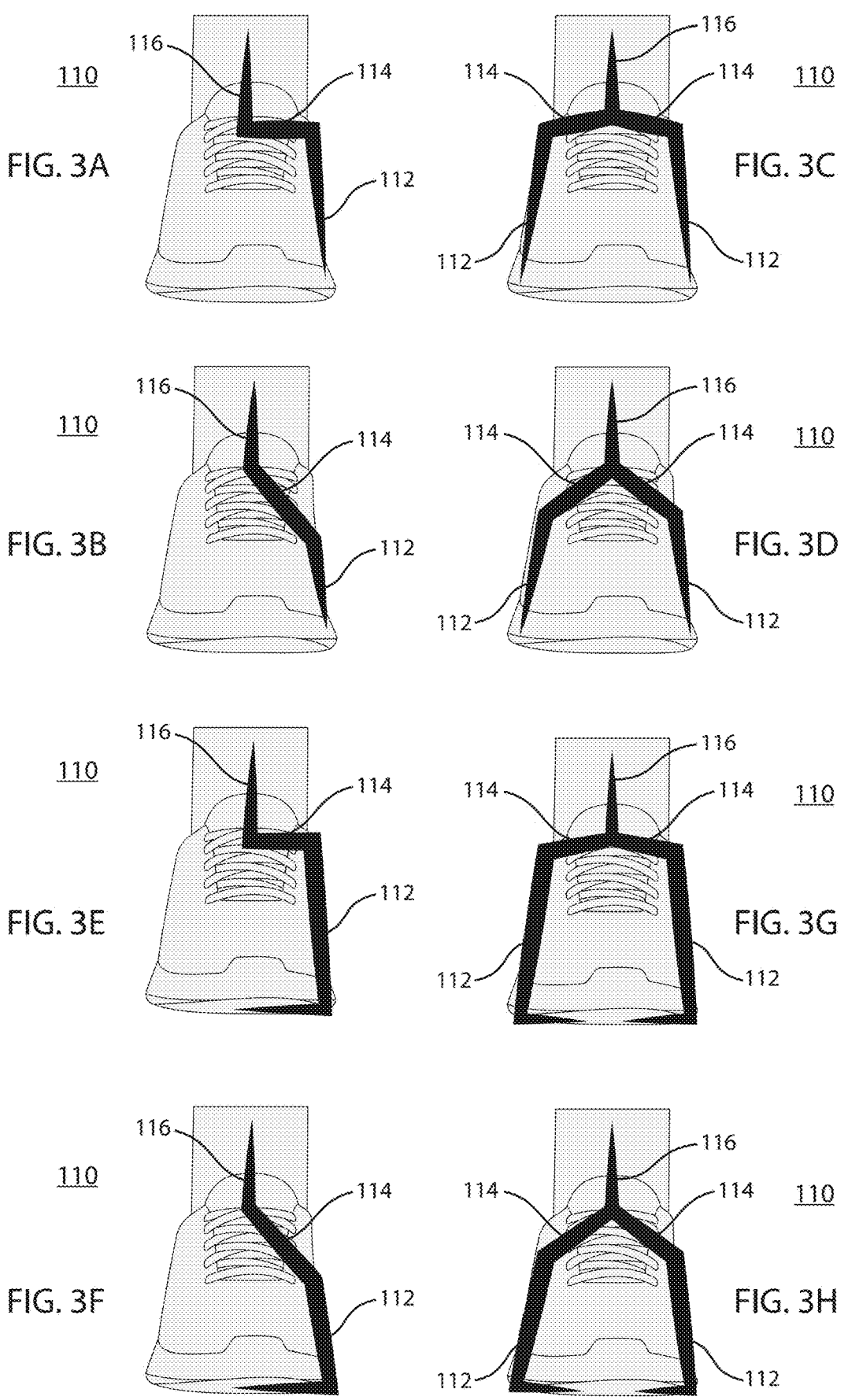

MOTION-ASSIST FOOTWEAR COMPRISING A FORCE TRANSLATOR

CROSS-REFERENCE TO RELATED APPLICATIONS

This application is a continuation of, claims priority to and the benefit of U.S. Ser. No. 17/827,949 filed May 30, 2022 and entitled "MOTION-ASSIST FOOTWEAR COMPRISING A FORCE TRANSLATOR." U.S. Ser. No. 17/827,949 is a continuation of, claims priority to and the benefit of PCT Serial No. PCT/US21/60404 filed Nov. 22, 2021 and entitled "MOTION-ASSIST FOOTWEAR COMPRISING A FORCE TRANSLATOR." PCT Serial No. PCT/US21/60404 claims the benefit of U.S. Provisional Patent Application No. 63/116,379, filed Nov. 20, 2020 and entitled "MOTION-ASSIST FOOTWEAR COMPRISING A FORCE TRANSLATOR." All of the aforementioned applications are incorporated herein by reference in their entireties.

FIELD

The present disclosure relates to footwear, and more particularly to motion-assist footwear comprising a force translator.

BACKGROUND

There is an ever-increasing need to enhance the performance characteristics of footwear. The present disclosure addresses this need.

SUMMARY

A motion-assist shoe in accordance with example embodiments of the present disclosure comprises an upper, a sole portion coupled to the upper, and a force translator comprising a base portion and a leg portion coupled by a dynamic portion. In example embodiments the base portion is coupled to the sole portion. In example embodiments the leg portion is configured to contact, and conform to, a leg above an ankle of a user of the shoe.

In example embodiments, the shoe comprises a stressed configuration in which the base portion and the leg portion are substantially perpendicular relative to each other.

In example embodiments, the shoe comprises an unstressed configuration in which the base portion and the leg portion are not substantially perpendicular relative to each other.

In example embodiments the dynamic portion is configured to bias the shoe toward the unstressed configuration to thereby bias a rearward portion of the sole portion upward relative to a forward portion of the sole portion.

BRIEF DESCRIPTION OF THE DRAWINGS

The accompanying drawings may provide a further understanding of example embodiments of the present disclosure and are incorporated in, and constitute a part of, this specification. In the accompanying drawings, only one motion-assist shoe (either a left shoe or a right shoe) may be illustrated, however, it should be understood that in such instances, the illustrated shoe may be mirror-imaged so as to be the other shoe. The use of like reference numerals throughout the accompanying drawings is for convenience only, and should not be construed as implying that any of the illustrated embodiments are equivalent. The accompanying drawings are for purposes of illustration and not of limitation.

FIGS. 3A-3H illustrate front views of example embodiments of a force translator of the present disclosure.

DETAILED DESCRIPTION

Figures 1A, 1B:
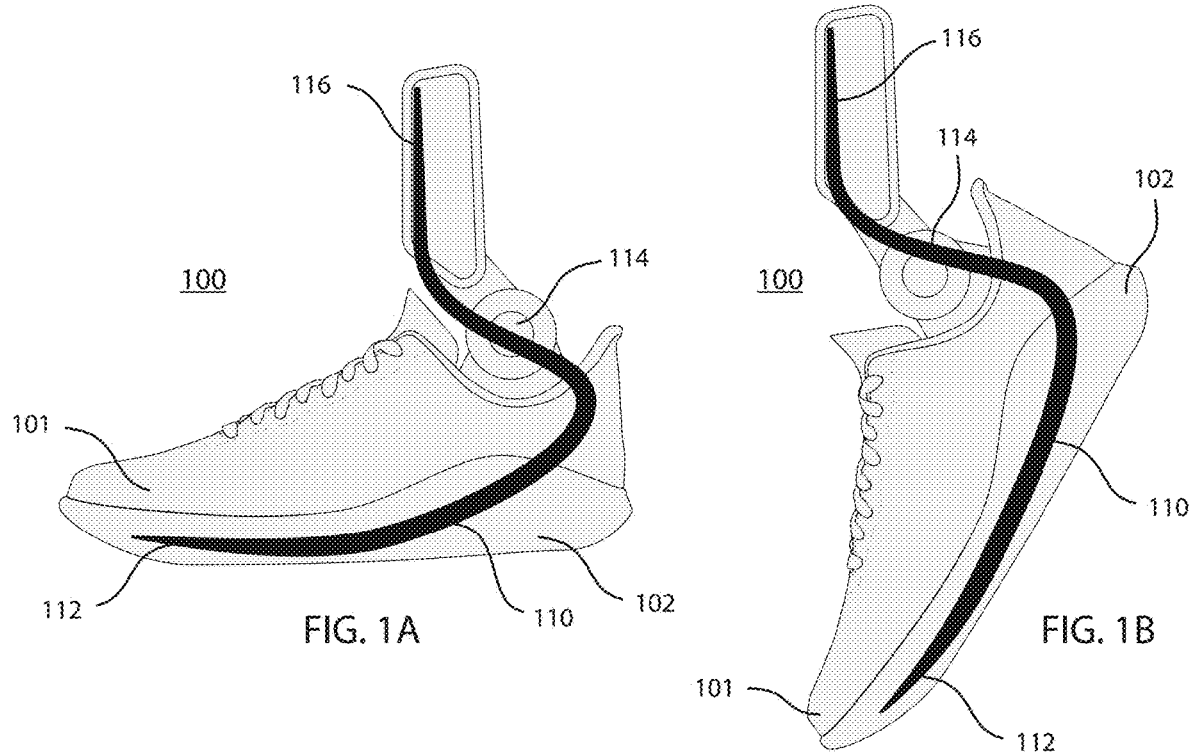
FIGS. 1A and 1B illustrate side views of an example embodiment of a motion-assist shoe, in stressed and unstressed configurations, respectively, wherein the force translator contacts the shin.

Example embodiments of the present disclosure are described in sufficient detail in this detailed description to enable persons having ordinary skill in the relevant art to practice the present disclosure, however, it should be understood that other embodiments may be realized and that mechanical and chemical changes may be made without departing from the spirit or scope of the present disclosure. Thus, this detailed description is for purposes of illustration and not of limitation.

For example, unless the context dictates otherwise, example embodiments described herein may be combined with other embodiments described herein. Similarly, references to "example embodiment," "example embodiments" and the like indicate that the embodiment(s) described may comprise a particular feature, structure, or characteristic, but every embodiment may not necessarily comprise the particular feature, structure, or characteristic. Moreover, such references may not necessarily refer to the same embodiment(s). Any reference to singular includes plural embodiments, and any reference to plural includes singular embodiments.

Any reference to coupled, connected, attached or the like may be temporary or permanent, removeable or not, non-integral or integral, partial or full, and may be facilitated by one or more of adhesives, stitches, hook and loop fasteners, buttons, clips, grommets, zippers and other means known in the art or hereinafter developed.

As used herein, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

No claim limitation is intended to invoke 35 U.S.C. 112(f) or pre-AIA 35 U.S.C. 112, sixth paragraph or the like unless it explicitly uses the term "means" and includes functional language.

In describing example embodiments of the motion-assist footwear, certain directional terms may be used. By way of example, terms such as "right," "left," "medial," "lateral," "front," "back," "forward," "backward," "rearward," "top," "bottom," "upper," "lower," "up," "down," and the like may be used to describe example embodiments of the motion-assist footwear. These terms should be given meaning according to the manner in which the motion-assist footwear is most typically designed for use, with the motion-assist footwear on a user's foot and with the user's shod foot disposed on or ready for placement on an underlying surface. Thus, these directions may be understood relative to the motion-assist footwear in such use. Similarly, as the motion-assist footwear is intended primarily for use as footwear, terms such as "inner," "inward," "outer," "outward," "innermost," "outermost," "inside," "outside," and the like should be understood in reference to the motion-assist footwear's intended use, such that inner, inward, innermost, inside, and the like signify relatively closer to the user's foot, and outer, outward, outermost, outside, and the like signify relatively farther from the user's foot when the motion-assist footwear is being used for its intended purpose. Notwithstanding the foregoing, if the foregoing definitional guidance is contradicted by an individual use herein of any of the foregoing terms, the term should be understood and read according to the definition that gives life and meaning to the particular instance of the term.

As used herein, unless the context dictates otherwise, a "sole portion" of a motion-assist shoe refers to an outsole or portions thereof, a midsole or portions thereof, an insole or portions thereof, a wedge or portions thereof, or other suitable structure disposed between and/or adjacent to the foregoing parts of a motion-assist shoe, for example, an insole or an internal cushion.

A motion-assist shoe in accordance with the present disclosure can be configured to augment or replicate a calf muscle at both shoe surface impact as well as shoe lift off, to thereby bias a shoe rearward portion upward relative to a shoe forward portion. A motion-assist shoe in accordance with the present disclosure may have particular utility in connection with a running shoe.

Figures 2A, 2B:
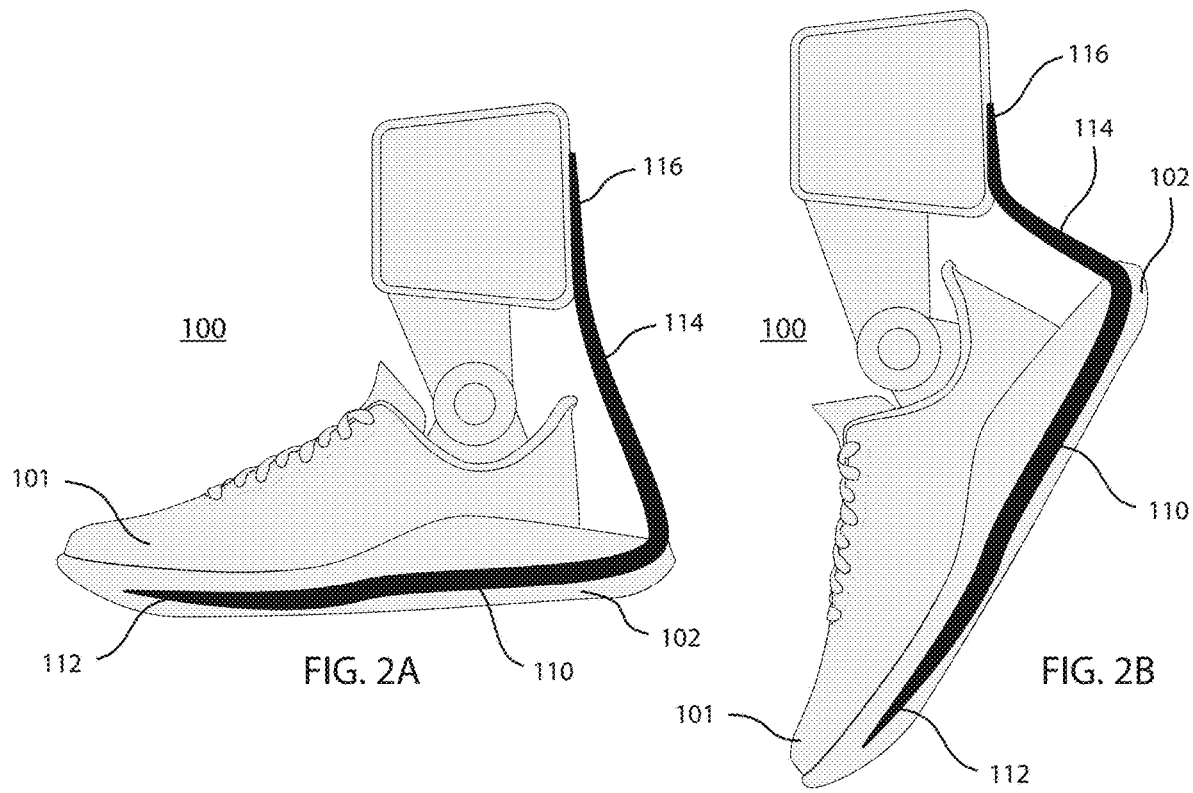
FIGS. 2A and 2B illustrate side views of an example embodiment of a motion-assist shoe, in stressed and unstressed configurations, respectively, wherein the force translator contacts the calf.

With reference to FIGS. 1A, 1B, 2A and 2B, a motion-assist shoe 100 in accordance with the present disclosure comprises an upper 101. A motion-assist shoe in accordance with the present disclosure further comprises a sole portion 102 coupled to the upper 101, the sole portion 102 comprising a forward portion (i.e., toward a forward most end of the motion-assist shoe 100) and a rearward portion (i.e., toward a rearward most end of the motion-assist shoe 100). In some embodiments, the rearward portion can be configured to be coterminous with a rearward most portion of the upper 101, e.g., as illustrated in FIGS. 1A and 1B). In other embodiments, the rearward portion can be configured to extend rearward beyond a rearward most portion of the upper 101, e.g., as illustrated in FIGS. 2A and 2B).

A motion-assist shoe 100 in accordance with the present disclosure still further comprises a force translator 110 comprising a base portion 112 and a leg portion 116 (e.g., extending vertically when the motion-assist shoe 100 is in a stressed configuration, as described below). In example embodiments, the base portion 112 and the leg portion 116 are coupled by a dynamic portion 114.

In example embodiments, the base portion 112, the leg portion 116 and the dynamic portion 114 are integral or unitary, while the dynamic portion retains at least one material property different from a corresponding material property of one or both the base portion and the leg portion. For example, the cross section of the dynamic portion 114 can be different (e.g., smaller, notched, grooved, perforated, twisted) than the cross section of the base portion 112 and/or the leg portion 116. For example, the force translator 110 can have a ribbon profile wherein the ribbon profile is twisted in the dynamic portion 114 (but not twisted or differently twisted in the base portion 112 and the leg portion 116) to permit resilient deformation of the dynamic portion 114 (but not in the base portion 112 and the leg portion 116, or to a lesser extent). Heat treating can also impart different characteristics to the dynamic portion 114.

A dynamic portion 114 can comprise a resiliently deformable material such as a spring, an s-spring, a shape-memory material or a stretch material (e.g., elastic). In example embodiments, the force translator 110 comprises a carbon fiber blade. In example embodiments, the force translator 110 transcends the ankle (and translates a force from below the ankle to above the ankle) but also allows the ankle to move and rotate. In this regard, in example embodiments, a motion-assist shoe 100 can comprise a point of rotation defined by an ankle. Additionally, in example embodiments the dynamic portion 114 of the force translator 110 is not directly coupled to any portion of the motion-assist shoe 100 nor is it configured to directly contact a foot, ankle or leg of a user of the motion-assist shoe 100. In this regard, FIGS. 3A-3H illustrate front views of example embodiments of a force translator of the present disclosure (although it will be apparent to those skilled in the art that the illustrated angles may be dampened for resilience (e.g., elimination of hot spots, stress and strain distribution), manufacturability (e.g., molding) and/or comfort).

In accordance with example embodiments of the present disclosure, the base portion 112 of the force translator 110 is coupled to the sole portion 102 (e.g., coupled to a side or embedded within the sole portion 102).

In accordance with some example embodiments of the present disclosure, the base portion 112 is coupled to a single side of the sole portion 102 (e.g., a lateral side or a medial side of the sole portion 102). In such embodiments, and with momentary reference to FIGS. 3A and 3B, the dynamic portion 114 can comprise an L shape with the leg portion 116 or comprise another angle or similar curve measured from the leg portion 116 to a lateral side or a medial side of the sole portion 102).

In accordance with other example embodiments of the present disclosure, the base portion 112 is coupled to both a lateral side and a medial side of the sole portion 102. In such embodiments, and with momentary reference to FIGS. 3C and 3D, the dynamic portion 114 can comprise a Y or T shape with the leg portion 116 or comprise another angle or similar curve measured from the leg portion 116 to two separate and distinct base portions 112 (one on or embedded within a lateral side and one on or embedded within a medial side of the sole portion 102).

In accordance with example embodiments of the present disclosure, the base portion 112 can be coupled to the sole portion under the footbed of the motion-assist shoe 100. For example, and with momentary reference to FIGS. 3E and 3F, the base portion can comprise an L shape or other angle or similar curve such that the base portion 112 extends from a side of the sole portion to under the footbed. In embodiments having two separate and distinct base portions 112, and with momentary reference to FIGS. 3G and 3H, each base portion 112 can comprise an L shape or other angle or similar curve to extend under the footbed.

In accordance with example embodiments of the present disclosure, the leg portion 116 of the force translator 110 is configured to contact, and conform to, a leg above an ankle of a user of the motion-assist shoe 100.

As an example, and with specific reference to FIGS. 1A and 1B, the leg portion 116 of the force translator 110 can be configured to contact, and conform to, a shin (e.g., at a shin pad to provide comfort to the user). In such embodiments, leg portion can be rounded or curved to conform to a shin. In such embodiments, dynamic portion 114 can be comprised of a resiliently deformable material such as a spring, an s-spring or a shape-memory material.

As another example, and with specific reference to FIGS. 2A and 2B, the leg portion 116 of the force translator 110 can be configured to contact, and conform to, a calf (e.g., secured with a strap extending circumferentially around a leg). In such embodiments, leg portion can be rounded or curved to conform to a calf. In such embodiments, dynamic portion 114 can be comprised of a resiliently deformable material such as a stretch material that elongates (and is configured to draw the base portion 112 and the leg portion 116 toward one another when the motion-assist shoe 100 is in a stressed configuration, as described below).

Figure 4:
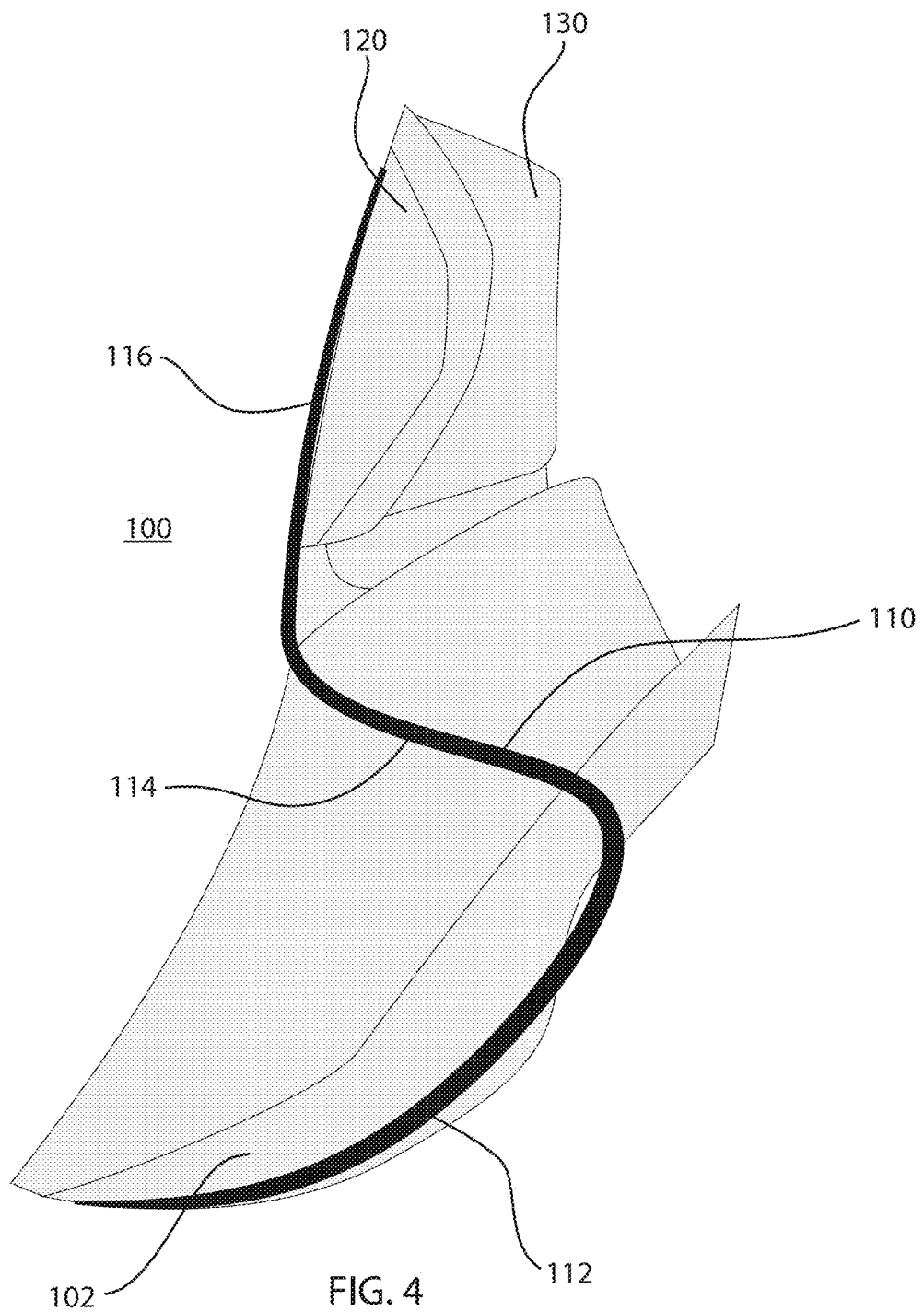
FIG. 4 illustrates side views of another example embodiment of a motion-assist shoe.

Another example embodiment of a motion-assist shoe 100 is described with reference to FIG. 4. Motion-assist shoe 100 comprises a force translator 110 having a base portion 112 and a leg portion 116, the base portion 112 and the leg portion 116 coupled by a dynamic portion 114. Motion-assist shoe 100 further comprises a semi-rigid shin pad 120 (e.g., to provide a resistance force against the shin) with a calf cuff 130 (e.g., to provide a pulling force on the calf). In the illustrated embodiments, the sole portion 102 has a curved profile (e.g., curved bottom surface) and the base portion 112 has a corresponding curved profile.

In accordance with example embodiments of the present disclosure, the motion-assist shoe 100 comprises a stressed configuration (e.g., FIGS. 1A and 2A) and an unstressed configuration (e.g., FIGS. 1B, 2B and 3). In accordance with example embodiments of the present disclosure, in the stressed configuration (e.g., FIGS. 1A and 2A), the base portion 112 and the leg portion 116 are substantially perpendicular relative to each other. In accordance with example embodiments of the present disclosure, in the unstressed configuration (e.g., FIGS. 1B, 2B and 3), the base portion 112 and the leg portion 116 are not substantially perpendicular relative to each other, e.g., are substantially parallel relative to each (or within 45, 30 or 15 degrees of being parallel to each other), albeit other along different axes.

In accordance with example embodiments of the present disclosure, the dynamic portion 114 of the force translator 110 is configured to bias the motion-assist shoe 100 toward the unstressed configuration to thereby bias the rearward portion upward relative to the forward portion. More specifically, in the stressed configuration, potential energy stored in the dynamic portion can urge the force translator 110 toward the unstressed configuration. In this regard, the motion-assist shoe 100 can be configured to augment or replicate a calf muscle at both shoe surface impact as well as shoe lift off, and thereby assist motion of the user and/or dampen impact during motion.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

I claim:

1. A motion-assist shoe comprising:
    an upper;
    a sole portion coupled to the upper, the sole portion comprising a forward portion and a rearward portion; and
    a force translator comprising a base portion and a leg portion, the base portion and the leg portion coupled by a dynamic portion;
    wherein the base portion, the leg portion and the dynamic portion are unitary one with another;
    wherein the base portion is coupled to the sole portion;
    wherein the leg portion is configured to contact, and conform to, a shin of a user of the shoe;
    wherein the shoe comprises a stressed configuration and an unstressed configuration;
    wherein, in the stressed configuration, the base portion and the leg portion are aligned at a first angle relative to each other;
    wherein, in the unstressed configuration, the base portion and the leg portion are aligned at a second angle relative to each other, the second angle being different from the first angle;
    wherein the dynamic portion is configured to bias the shoe toward the unstressed configuration to thereby bias the rearward portion upward relative to the forward portion; and
    wherein the dynamic portion is comprised of a resiliently deformable material.

2. The motion-assist shoe of claim 1, wherein the dynamic portion is not directly coupled to any portion of the motion-assist shoe.

3. The motion-assist shoe of claim 1, wherein the dynamic portion has at least one material property different from a corresponding material property of both the base portion and the leg portion.

4. A motion-assist shoe comprising:
    an upper;
    a sole portion coupled to the upper, the sole portion comprising a forward portion and a rearward portion; and
    a force translator comprising a base portion and a leg portion, the base portion and the leg portion coupled by a dynamic portion;
    wherein the leg portion is configured to contact, and conform to, a leg above an ankle of a user of the shoe;
    wherein the shoe comprises a stressed configuration and an unstressed configuration;
    wherein, in the stressed configuration, the dynamic portion is resiliently elongated and the base portion and the leg portion are at a first angle relative to each other;
    wherein, in the unstressed configuration, the dynamic portion is not resiliently elongated and the base portion and the leg portion are at a second angle relative to each other, the second angle being different from the first angle;
    wherein the dynamic portion is configured to bias the shoe toward the unstressed configuration to thereby bias the rearward portion upward relative to the forward portion;

wherein the rearward portion of the sole portion extends rearward beyond a rearward-most portion of the upper; and wherein the force translator extends from the sole portion at a position rearward of the rearward-most portion of the upper.

5. The motion-assist shoe of claim 4, wherein the dynamic portion is comprised of a resiliently deformable material.

6. The motion-assist shoe of claim 4, wherein the dynamic portion is not directly coupled to any portion of the motion-assist shoe.

7. The motion-assist shoe of claim 4, wherein the dynamic portion is comprised of a stretch material, and the leg portion is configured to contact, and conform to a calf of a user.

8. The motion-assist shoe of claim 4, wherein the dynamic portion has at least one material property different from a corresponding material property of both the base portion and the leg portion.

9. A motion-assist shoe comprising:
an upper;
a sole portion coupled to the upper, the sole portion comprising a forward portion and a rearward portion; and
a force translator comprising a base portion and a leg portion, the base portion and the leg portion coupled by a dynamic portion;
wherein the leg portion is configured to contact, and conform to, a leg above an ankle of a user of the shoe;
wherein the shoe comprises a stressed configuration and an unstressed configuration;
wherein, in the stressed configuration, the dynamic portion is resiliently deformed and the base portion and the leg portion are at a first angle relative to each other;
wherein, in the unstressed configuration, the dynamic portion is not resiliently deformed and the base portion and the leg portion are at a second angle relative to each other, the second angle being different from the first angle;
wherein the dynamic portion is configured to bias the shoe toward the unstressed configuration to thereby bias the rearward portion upward relative to the forward portion; and
wherein the dynamic portion extends between a rearward portion of the base portion of the force translator and a forward portion of the leg portion of the force translator.

10. The motion-assist shoe of claim 9, wherein the force translator extends across at least a portion of a medial side of the motion-assist shoe.

11. The motion-assist shoe of claim 9, wherein the force translator extends across at least a portion of a lateral side of the motion-assist shoe.

12. The motion-assist shoe of claim 9, wherein the force translator extends across at least a portion of a lateral side portion and a medial side of the motion-assist shoe.

13. The motion-assist shoe of claim 12, wherein the force translator bifurcates from the leg portion and extends across the lateral side portion and the medial side of the motion-assist shoe.

14. The motion-assist shoe of claim 9, wherein the force translator extends across a hinge when the shoe is in the stressed configuration.

15. The motion-assist shoe of claim 14, wherein the force translator is off-center of the hinge when the shoe is in the unstressed configuration.

16. The motion-assist shoe of claim 15, wherein the force translator passes rearward of the hinge when the shoe is in the unstressed configuration.

17. The motion-assist shoe of claim 16, wherein the force translator is a resiliently deformable material.

18. The motion-assist shoe of claim 9, wherein the force translator extends around a side of the sole portion and under a footbed.

* * * * *